United States Patent [19]

Habicht

[11] 4,176,190
[45] Nov. 27, 1979

[54] DIURETIC AND SALIURETIC SULPHAMOYLBENZOIC ACIDS

[75] Inventor: Ernst Habicht, Oberwil, Switzerland

[73] Assignee: Ciba-Geigy Corporation, Ardsley, N.Y.

[21] Appl. No.: 860,533

[22] Filed: Dec. 14, 1977

[30] Foreign Application Priority Data

Dec. 24, 1976 [CH] Switzerland ............... 16309/76

[51] Int. Cl.² .................. A61K 31/40; C07D 207/32
[52] U.S. Cl. ..................... 424/274; 260/326.41;
260/556 C; 260/326.5 SF
[58] Field of Search .............. 260/326.41, 239.6;
424/274

[56] References Cited

U.S. PATENT DOCUMENTS

| | | | |
|---|---|---|---|
| 3,534,027 | 10/1970 | Czyzewski et al. | 260/239.65 |
| 3,565,920 | 2/1971 | Werner | 260/347.2 |
| 3,939,267 | 2/1976 | Werner | 424/319 |
| 4,010,273 | 3/1977 | Bormann et al. | 424/274 |
| 4,082,851 | 4/1978 | Feit et al. | 424/300 |
| 4,093,735 | 6/1978 | Bormann et al. | 424/274 |

Primary Examiner—Donald G. Daus
Assistant Examiner—Diana G. Rivers
Attorney, Agent, or Firm—Theodore O. Groeger

[57] ABSTRACT

The invention relates to sulphamoylbenzoic acids of the formula

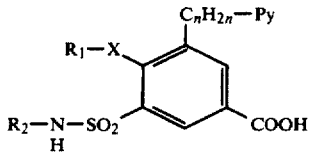

in which $R_1$ is a substituted or unsubstituted aryl radical, X is oxygen or sulphur, $R_2$ is hydrogen, lower alkyl or oxa-lower alkyl or an aryl radical, Py is a substituted or unsubstituted 1-pyrrolyl radical and n is an integer from 0 to 4, and salts of these compounds.

They are valuable diuretics and saliuretics.

10 Claims, No Drawings

DIURETIC AND SALIURETIC SULPHAMOYLBENZOIC ACIDS

The invention relates to sulphamoylbenzoic acids, especially to 3-sulphamoyl-5-pyrrolyl-alkylbenzoic acids which are substituted in the 4-position and are of the formula I

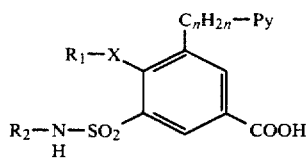

in which $R_1$ is a substituted or unsubstituted aryl radical, X is oxygen or sulphur, $R_2$ is hydrogen, lower alkyl or oxa-lower alkyl or an aryl radical, Py is a substituted or unsubstituted 1-pyrrolyl radical and n is an integer from 0 to 4, and salts of such compounds, as well as processes for their preparation and also to pharmaceutical formulations which contain such compounds and the pharmaceutical use of these formulations.

The aryl radical $R_1$ and the radical $R_2$, when the latter is not hydrogen, lower alkyl or oxa-lower alkyl, are preferably phenyl or phenyl radicals substituted by lower alkyl, lower alkoxy, halogen, trifluoromethyl, nitro and/or amino groups. Each of the phenyl radicals preferably contains up to two identical or different substituents, which can be in any position.

A substituted 1-pyrrolyl radical Py is preferably substituted by lower alkyl radicals, preferably in the 3-position and/or 4-position.

In the alkylene radical $C_nH_{2n}$, n preferably differs from 0.

In the context of the present description, organic radicals designated as "lower" contain up to 7, and especially up to 4, carbon atoms.

Lower alkyl is especially methyl, as well as ethyl, n-propyl, isopropyl, n-butyl, isobutyl or tert.-butyl and also n-pentyl, neopentyl, n-hexyl or n-heptyl.

Lower alkoxy is in particular methoxy, as well as ethoxy, n-propoxy, isopropoxy, n-butoxy, isobutoxy or t-butoxy and also n-pentyloxy, n-hexyloxy or n-heptyloxy.

Oxa-lower alkyl is preferably lower alkoxymethyl, for example methoxymethyl or ethoxymethyl.

Halogen is especially chlorine, as well as fluorine or bromine and also iodine.

Amino groups are primary and also secondary or tertiary amino groups; the latter are especially mono- or di-lower alkylamino groups.

Salts of compounds of the formula I are metal salts or ammonium salts, especially those with alkali metal or alkaline earth metal ions or with ammonia or monovalent, divalent or polyvalent primary, secondary or tertiary amines or quaternary ammonium ions, or also salts with anion exchangers.

The compounds of the present invention have valuable pharmacological properties or can be used as intermediates for the preparation of compounds having such properties.

Thus, the compounds, according to the invention, of the formula I show a dosage-dependent, long-term increase in diuresis and saliuresis in dogs when administered in the dosage range of from 0.1 mg/kg perorally. It is also particularly interesting that, from a dosage level which corresponds to about 10 times the normal dosage, the potassium uresis, is no longer substantially increased even by a considerable further increase in the dose, so that the tendency to a shift in the electrolyte metabolism is reduced even when excessive doses are used.

The novel compounds are therefore valuable diuretics and saliuretics and, on enteral, for example oral, and parenteral administration can be used for the treatment of, for example, high blood pressure and of disorders in the electrolyte metabolism and water metabolism in the body and especially for the treatment of cardiac, renal and other edema and, if appropriate, the novel compounds can be administered in combination with other pharmacologically active substances, such as antihypertensive agents, for example reserpine, Clonidin, α-methyldopa, Guanethidin, Oxprenolol, hydralazine or dihydralazine.

The invention relates in particular to compounds of the formula I in which Py is 1-pyrrolyl which is unsubstituted or substituted in the 3-position and/or 4-position by lower alkyl, for example methyl, n is an integer from 1 to 4, $R_1$ is phenyl, lower alkylphenyl, such as methylphenyl, lower alkoxyphenyl, such as methoxyphenyl, or halogenophenyl, for example chlorophenyl, X is oxygen or sulphur and $R_2$ is hydrogen or lower alkyl, for example methyl, and salts, especially pharmaceutically usable metal salts, such as alkali metal or alkaline earth metal salts, or ammonium salts of such compounds.

The invention relates in particular to compounds of the formula I in which Py is 1-pyrrolyl, n is an integer from 1–3 and in particular is 2 or 3, $R_1$ is phenyl, X is oxygen or, preferably, sulphur and $R_2$ is hydrogen, and salts, especially pharmaceutically usable metal salts, such as alkali metal or alkaline earth metal salts, or ammonium salts of such compounds.

The compounds, according to the invention, of the formula I can be prepared in a manner which is known per se, for example by converting $R_o$ in a compound of the formula

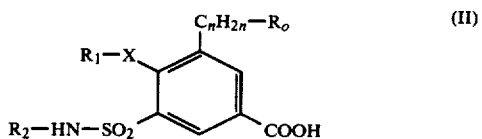

in which $R_o$ is a group which can be converted into a substituted or unsubstituted 1-pyrrolyl radical Py, or in a salt thereof, into a substituted or unsubstituted 1-pyrrolyl radical Py, and, if desired, converting a compound of the formula I, obtainable according to the invention, into another compound of the formula I and/or, if desired, converting a resulting salt into the free compound or into another salt, and/or converting a resulting free compound into a salt.

Salts of starting materials of the formula II which can be used are metal salts or ammonium salts or, if $R_o$ is a basic group, also acid addition salts, such as salts of mineral acids, for example hydrochloric acid, and also inner salts.

Starting compounds of the formula II which can be used according to the invention are preferably those in which $R_o$ is a primary amino group. These compounds are reacted, for example, with a substituted or unsubstituted 1,4-dioxobutane or a reactive carbonyl derivative thereof, it also being possible to employ a 1,4-dioxobutane, or a derivative thereof, in the form of an enol derivative, such as of an enol ether, for example an enol lower alkyl ether, or an enol ester, for example an enol lower alkanoyl ester. A reactive carbonyl derivative of a substituted or unsubstituted 1,4-dioxo-butane is understood as meaning a compound which reacts as such with the starting material of the formula II, in which $R_o$ is amino, with the formation of the 1-pyrrolyl group, or which is transformed or converted, under the reaction conditions, into the 1,4-dioxo-butane on which it is based or into another reactive 1,4-dioxo-butane compound and can then enter into reaction with the starting material of the formula II in which $R_o$ is amino, with the formation of a substituted or unsubstituted 1-pyrrolyl group.

Reactive carbonyl derivatives of a substituted or unsubstituted 1,4-dioxo-butane are, for example, geminal addition compounds, such as corresponding hydrates, halogenohydrins, for example chlorohydrins or bromohydrins, cyanohydrins or metal compounds, such as alkali metal compounds or alkaline earth metal compounds, for example sodium bisulphite compounds.

Preferred reactive carbonyl derivatives of a substituted or unsubstituted 1,4-dioxo-butane are the acetals and acylals thereof and also corresponding thio compounds (thioacetals or thioacylals) or amino compounds (aminals), as well as mixed derivatives of this type. Acetals comprise monoacetals or diacetals and corresponding hemiacetals, and also anhydrides of hemi-acetals, and acylals comprise the corresponding acylal compounds. Mixed derivatives of this type are, for example, geminal halogenoethers, especially α-chloro- and α-bromo-ethers. Anhydrides of hemi-acetal and hemi-acylal compounds are, especially, corresponding tetrahydrofurane compounds which have an etherified or esterified hydroxyl group in the 2-position and 5-position. Etherified hydroxyl groups in acetal compounds are, in particular, lower alkoxy groups, for example methoxy or ethoxy groups, whilst in acylal compounds esterified hydroxyl groups are, in particular, lower alkanoyloxy groups, for example acetoxy groups, benzoyloxy groups or halogen, especially chlorine or bromine. Acetal compounds which can preferentially be employed as reactive derivatives of a 1,4-dioxo-butane are substituted or unsubstituted 2,5-di-lower alkoxy-tetrahydrofuranes, for example 2,5-dimethoxy- or 2,5-diethoxy-tetrahydrofurane.

Further reactive carbonyl derivatives of a substituted or unsubstituted 1,4-dioxo-butane are corresponding unsubstituted or N-substituted, and especially N-hydroxysubstituted or N-lower alkoxy-substituted, imino compounds, and also substituted or unsubstituted 2,3,4,5-tetrahydroxy-adipic acids, especially those which, under the reaction conditions, are converted, with the loss of 2 mols of water, via unstable α-ketocarboxylic acids, with the loss of 2 mols of carbon dioxide, into corresponding 1,4-dioxobutane compounds, for example into succinaldehyde in the case of mucic acid, which compounds, with the amino group $R_o$ of the starting material of the formula II, form a substituted or unsubstituted 1-pyrrolyl radical.

The abovementioned addition and substitution derivatives of substituted or unsubstituted 1,4-dioxobutanes or their enol tautomers can be prepared in a manner which is known per se, if desired directly prior to or in the course of the process according to the invention, and such derivatives can be so reactive and/or unstable that prior isolation thereof is not necessary or is inappropriate.

Examples of possible 1,4-dioxobutanes which can be employed according to the invention are substituted or unsubstituted succinaldehydes, especially succinaldehyde, 2-methyl- and 2,3-dimethyl-succinaldehyde, or levulinaldehyde, and examples of possible addition and/or substitution derivatives of substituted or unsubstituted 1,4-dioxobutanes which can be isolated and can be employed according to the invention are 1,1,4,4-tetra-lower alkoxybutanes, for example succinaldehyde-bis-dimethylacetal (i.e. 1,1,4,4-tetramethoxybutane) and succinaldehyde-mono-diethylacetal; anhydro(succinaldehyde-bis-mono-lower alkyl-acetals), for example 2,5-dimethoxytetrahydrofurane; the bis-bisulphite adduct of succinaldehyde; butane-1,4-dioxime and its 0-methyl compounds; succinaldehyde-cyanohydrin; succinaldehyde-bis-aminals, for example 1,2-bis(1,3-diphenyl-2-imidazolidinyl)-ethane; acylals, such as succinaldehyde monohydrate diacetate (i.e. 4,4-diacetoxybutyraldehyde) and 2,5-diacetoxytetrahydrofurane or 2,5-dibromotetrahydrofurane; enol-ethers, such as 1,4-diphenoxybutadiene and enol-esters, such as 1,4-diacetoxybutadiene. An example of a mixed derivative of this type which can be employed is 2-chloro-5-allyloxy-tetrahydrofurane.

The reaction according to the invention is carried out in a manner which is known per se, in the presence or absence of a solvent and/or of an additional reagent which is capable, for example, of converting a derivative of a 1,4-dioxo-butane into the reactive form, such as of an acid, and, if necessary, with cooling or warming, in a closed vessel and/or in an inert gas atmosphere, such as a nitrogen atmosphere. Thus, for example, a starting material of the formula II can be reacted with a substituted or unsubstituted succinaldehyde, or an acetal thereof, especially with a 2,5-disubstituted tetrahydrofurane which contains an etherified hydroxyl group in the 2-position and in the 5-position, such as 2,5-dimethoxytetrahydrofurane, for example by warming in glacial acetic acid, analogously to the process developed by N. Clauson-Kaas and Z. Tyle, Acta Chem. Scand. 6, 667 (1952) and 6, 867 (1952).

The substituted or unsubstituted 1,4-dioxobutanes and derivatives which are required according to the process are known or can be prepared in a manner which is known per se.

The starting materials of the formula II in which n is 2-4 can be obtained, for example, when compounds of the formula II in which $R_o$ is an amino group and n is 0, which compounds are accessible by the method of P. W. Feit, J. Med. Chem. 14, 432 (1971), are converted into the diazonium chlorides and the latter are reacted with a suitable olefinic carboxylic acid derivative, preferably a corresponding amide or nitrile, for example acrylamide, acrylonitrile or methacrylamide, at temperatures of preferably below 50° C. and in the presence of a suitable catalyst, for example copper-II chloride. The chlorine is eliminated in a known manner, for example by reduction with zinc and glacial acetic acid, from the 2-chloro-2-carbamoylalkyl or 2-chloro-2-cyanoalkyl compounds thus formed. The 2-cyanoalkyl or 2-carbamoylalkyl compounds which form can then either be subjected to acid amide degradation, for example by the method of Hoffmann or Schmidt, the alkyl chain being shortened by one carbon atom, or can be converted into amines of the formula II by reducing the nitrile or amide group, for example by treatment with hydrogen in the presence of platinum oxide in glacial acetic acid or with Raney nickel. Amines of the formula II in which n is 2, 3 or 4 are readily accessible in this way.

Amines of the formula II in which n is 1 can preferably be obtained by reacting the abovementioned diazonium salts with an alkali metal cyanide by a Sandmeyer reaction and subsequently reducing the resulting nitrile, or by reacting the diazonium salts with formaldoxime by the method of W. F. Beech, J. Chem. Soc., 1954,1,297, the aldoxime formed further being converted, under the reaction conditions and with the elmination of water, into the abovementioned nitrile, which can be reduced, as indicated above.

A variant of the above process comprises the reaction of a compound of the formula II in which $R_o$ is a sulphineimino group with a substituted or unsubstituted butadiene, for example butadiene itself or a lower alkyl-substituted butadiene, such as 2,3-dimethylbutadiene.

This reaction is carried out in a manner which is known per se, for example in the presence of a base, such as of an alkali metal hydroxide, for example sodium hydroxide or potassium hydroxide, preferably in the presence of an inert solvent, such as of a lower alkanol, for example methanol or ethanol, or of an ether, such as dioxane or tetrahydrofurane, and, if necessary, with cooling or warming, in a closed vessel and/or in an inert gas atmosphere, for example a nitrogen atmosphere. An intermediate of the formula II in which $R_o$ is a substituted or unsubstituted 1-oxido-3,6-dihydro-1,2-thiazin-1-yl radical forms under the reaction conditions. An intermediate product of this type is converted under the reaction conditions, for example on warming in the presence of bases, preferably of alkali metal hydroxides, with the elimination of sulphur dioxide and hydrogen sulphide, into the compounds, according to the invention, of the formula I.

The starting materials can be obtained, for example, by treating compounds of the formula II in which $R_o$ is amino with thionyl chloride.

According to a further process, compounds of the formula I in which n differs from O are also obtained according to the invention when a compound of the formula II in which $R_o$ is a reactive esterified hydroxyl group is reacted with a salt of a substituted or unsubstituted pyrrole.

A reactive esterified hydroxyl group $R_o$ is a hydroxyl group esterified by a strong acid, for example an inorganic acid, such as a strong mineral acid, for example a hydrogen halide acid, or a strong organic acid, such as a corresponding organic sulphonic acid, for example a lower alkanesulphonic acid or a preferably substituted benzenesulphonic acid. In this case, $R_o$ is, in particular, halogen, for example chlorine, bromine or iodine, or lower alkyl-sulphonyloxy, for example methylsulphonyloxy, or substituted or unsubstituted phenylsulphonyloxy, for example 4-methylphenylsulphonyloxy, 4-bromophenylsulphonyloxy or 3-nitrophenylsulphonyloxy. A salt of a substituted or unsubstituted pyrrole is, for example, a metal salt, especially a potassium salt.

The reaction is carried out in a manner which is known per se, for example in the absence or presence of a solvent, such as in an anhydrous, polar, non-acid, preferably aprotic solvent, for example dimethylformamide or hexamethylphosphoric acid triamide, if necessary with cooling or warming, in a closed vessel and/or in an inert gas atmosphere, for example a nitrogen atmosphere.

The starting materials of the formula II in which $R_o$ is an esterified hydroxyl group can be obtained, for example, when the amino group in compounds of the formula II in which $R_o$ is amino is converted, for example via the diazonium group, into the hydroxyl group and the latter is converted into the esterified hydroxyl group $R_o$ by esterification, for example by treatment with a halogenating agent, for example thionyl chloride, or with an organic sulphonyl chloride.

A further process for the preparation of the compounds of the formula I comprises the conversion of the group A in a compound of the formula

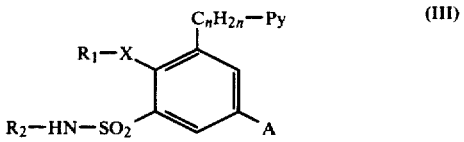

in which A is a functionally modified carboxyl group, into the free carboxyl group and, if desired, carrying out the additional steps indicated above.

The group A is, especially, an esterified carboxyl group, such as lower alkoxy-carbonyl, or an α-phenyl-lower alkoxy-carbonyl, for example methoxycarbonyl, ethoxycarbonyl, benzyloxycarbonyl or diphenylmethoxycarbonyl, and also an amidated carboxyl group, such as unsubstituted or N-substituted carbamoyl, or cyano.

The above conversion of a group A into the free carboxyl group is effected in a manner which is known per se, for example by solvolysis, especially hydrolysis in an acid medium or, preferably, in a weakly alkaline medium, or, if a starting material of the formula III is employed in which A is an α-aryl-lower alkyl group, by reduction, in particular by treatment with hydrogen in the presence of a suitable hydrogenation catalyst, preferably palladium, palladium-on-charcoal or palladium-on-barium sulphate.

The starting materials of the formula III can be prepared in a manner which is known per se, for example by the above process using compounds of the formula II in which $R_o$ in particular is amino and in which a functionally modified carboxyl group, such as an esterified or amidated carboxyl group, or cyano is present in place of the free carboxyl group, as the starting materials.

A further process for the preparation of the compounds, according to the invention, of the formula I comprises the reaction of a pyrrolyl derivative of the formula

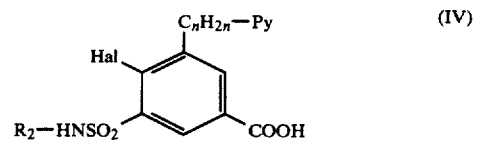

in which Hal is halogen, with a compound of the formula $R_1—X—M$ (V), in which M is hydrogen or a metal ligand, and, if desired, carrying out the additional steps indicated above.

A halogen atom Hal is, for example, fluorine, chlorine or bromine, whilst a metal ligand M in particular is an alkali metal, especially sodium.

The above reaction is carried out in a manner which is known per se and is preferably carried out in the presence of a strongly polar aprotic solvent, for example hexamethylphosphoric acid diamide, and at elevated temperatures, for example above 100° C. and preferably at 130°–160°, and in an inert gas atmosphere.

The starting materials of the formula IV can be prepared in a manner which is known per se, for example by the above process using compounds of the formula II in which $R_o$ in particular is amino and in which a halogen Hal is present in place of the group $R_1$—X—, as the starting materials. A suitable starting material of this type is, for example, 3-sulphamoyl-4-chloro-5-aminobenzoic acid, which has been described by P. W. Feit et al., J. Med. Chem. 13,1,071 (1970).

Compounds of the formula I which are obtainable according to the invention can be converted into other compounds of the formula I in a manner which is known per se. Thus, in compounds of the formula I, a hydrogen atom $R_2$ located on the sulphamoyl nitrogen atom can be replaced by a lower alkyl or lower alkoxy-lower alkyl radical by means of alkylation processes which are known per se, or by a lower alkoxy-methyl radical by treatment with formaldehyde in the presence of a lower alkanol, or, in a compound of the formula I in which $R_2$ is the methoxymethyl group, the methoxy group can be converted into a corresponding lower alkoxy-methyl group by treatment with another lower alkanol.

Free compounds obtainable according to the invention can be converted into their salts in a manner which is known per se, for example by treatment with a metal salt-forming reagent, such as an alkali metal or an alkali metal compound, for example an alkali metal hydride, alkali metal amide, alkali metal oxide or alkali metal hydroxide, an alkali metal carbonate or alkali metal bicarbonate or a suitable alkali metal salt of an organic carboxylic acid, for example sodium α-ethyl-caproate, or with ammonia, an amine or a suitable cation exchanger.

Resulting salts can be converted into the free compound in a manner which is known per se, for example by treatment with an acid reagent, for example a mineral acid.

The invention also relates to those embodiments of the process in which a compound obtainable as an intermediate at any process stage is used as the starting material and the missing process steps are carried out, or in which a starting material is formed under the reaction conditions or is used in the form of a derivative thereof, if appropriate in the form of a salt.

The starting materials used in the process of the present invention are preferably those which result in the compounds described initially as being particularly valuable.

The present invention also relates to pharmaceutical formulations which contain compounds of the formula I or pharmaceutically usable salts thereof. The pharmaceutical formulations according to the invention are those for enteral, such as oral or rectal, and also parenteral administration to warm-blooded animals and contain the pharmacological active compound on its own or together with a pharmaceutically usable excipient. The dosage of the active compound depends on the species of the warm-blooded animal, the age and the state of health of the individual and also on the mode of administration.

The novel pharmaceutical formulations contain from about 10% to about 95%, and preferably from about 20% to about 90%, of the active compound. Pharmaceutical formulations according to the invention are, for example, in the form of dosage units, such as dragées, tablets, capsules, suppositories or ampoules.

The pharmaceutical formulations of the present invention are prepared in a manner which is known per se, for example by means of conventional mixing, granulating, dragée-making, dissolving or lyophilising processes. Thus, pharmaceutical formulations for oral use can be obtained by combining the active compound with solid excipients, granulating a resulting mixture if desired and processing the mixture or granules, after adding suitable auxiliaries if desired or necessary, to give tablets or dragée cores.

Suitable excipients are, especially, fillers, such as sugars, for example lactose or sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose, hydroxypropyl-methylcellulose, sodium carboxymethylcellulose and/or polyvinylpyrrolidone, and/or, if desired, disintegrating agents, such as the above-mentioned starches, and also carboxymethyl-starch, crosslinked polyvinylpyrrolidone, agar or alginic acid or a salt thereof, such as sodium alginate. Auxiliaries are, in particular, flow control agents and lubricants, for example silica, talc, stearic acid or salts thereof, such as magnesium stearate or calcium stearate, and/or polyethylene glycol. Dragée cores are provided with suitable coatings which, if desired, are resistant to gastric juices, and for this purpose, inter alia, concentrated sugar solutions, which can contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyes or pigments can be added to the tablets or dragée coatings, for example for identification or in order to characterise different doses of the active compound.

Other pharmaceutical formulations which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and can contain stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, naturally or synthetic triglycerides, paraffin hydrocarbons, polyethylene glycols or higher alkanols. In addition, it is also possible to use gelatine rectal capsules which consist of a combination of the active compound with a base; bases which can be used are, for example, liquid triglycerides, polyethylene glycols or paraffin hydrocarbons.

Formulations suitable for parenteral administration are, in particular, aqueous solutions of an active compound in the water-soluble form, for example of a water-soluble salt, and also suspensions of the active compound, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

The examples which follow illustrate the invention described above; however, they are not intended to restrict the scope of the invention in any way. Temperatures are given in degrees centigrade.

EXAMPLE 1

3-Sulphamoyl-4-phenoxy-5-[1-pyrrolyl]-benzoic acid

A mixture of 3-sulphamoyl-4-phenoxy-5-amino-benzoic acid (3.08 g=10 mmols); P. W. Feit, J. Med. Chem. 14,432 (1971), 2,5-dimethoxy-tetrahydrofurane (1.32 g=10 mmols) and 5 ml of glacial acetic acid is refluxed for 15 minutes in an oil bath and evaporated to dryness in vacuo and the residue is recrystallised from ethyl acetate; the compound melts at 209°–210° C.

EXAMPLE 2

3-Sulphamoyl-4-phenoxy-5-[β-(1-pyrrolyl)-ethyl]-benzoic acid

A suspension of 3-sulphamoyl-4-phenoxy-5-[β-amino-ethyl]-benzoic acid hydrochloride (1.86 g=5 mmols) in 10 ml of hexamethylphosphoric acid triamide (hexametapol) is brought into solution at 90°–100°, 2,5-dimethoxytetrahydrofurane (0.7 g=5.5 mmols) is added and the mixture is reacted at this temperature for 20 minutes. After cooling, pouring into water, acidifying with glacial acetic acid and extracting with ethyl acetate, drying the solution with sodium sulphate and filtering through silica gel, evaporating the filtrate and twice taking up the residue in benzene and evaporating, a brown resin is obtained and this is taken up in 20 ml of benzene and, after adding 5 ml of cyclohexane, filtered off and brought to crystallisation using further cyclohexane. The crude product (melting point 205°–209°, decomposition) is purified by repeated recrystallisation from ethyl acetate/cyclohexane: melting point 216°–218° (decomposition).

The starting material 3-sulphamoyl-4-phenoxy-5-[β-aminoethyl]-benzoic acid hydrochloride is obtained as follows:

A solution prepared from 3-sulphamoyl-4-phenoxy-5-amino-benzoic acid (15.6 g=50 mmols; P. W. Feit, J. Med. Chem. 14, 432 (1971)), glacial acetic acid (50 ml) and concentrated hydrochloric acid (12 ml) is diazotised (for 15 minutes) at 0°–5° C. by the dropwise addition of a solution of sodium nitrite (3.5 g) in 25 ml of water, the reaction mixture is stirred for a further 30 minutes, a solution of acrylamide (3.55 g=50 mmols) in 40 ml of acetone is added and immediately thereafter 2.5 g of copper-II chloride (CuCl$_2$.2H$_2$O) are added and the olive green solution is warmed as rapidly as possible to 40°, whereupon a slightly exothermic reaction takes place and a vigorous evolution of nitrogen starts. The temperature is kept at 40°–45° C. by means of a cooling bath. After the evolution of nitrogen has ended (15 minutes), the mixture is kept at 40° C. for a further 30 minutes. Acetone, water and glacial acetic acid are then removed in vacuo. The resinous residue is extracted with 2 N hydrochloric acid and ethyl acetate, the two phases are separated and the aqueous phase is twice extracted by shaking with ethyl acetate. After washing with water, the ethyl acetate phase is dried and filtered and the filtrate is evaporated: crude 3-sulphamoyl-4-phenoxy-5-[β-carbamoyl-β-chloroethyl]-benzoic acid, which is further processed without further purification:

8.5 g of the above crude product, dissolved in 25 ml of glacial acetic acid, are stirred with 4 g of zinc dust, initially at room temperature and then for 3 hours at 80°–85°, the excess zinc dust is filtered off and washed with glacial acetic acid and the solution is evaporated in vacuo. The zinc dust is dissolved in dilute hydrochloric acid and the flocks which remain after filtering off and washing with water are combined with the other crude product.

The combined, dried residues are taken up in a little ethyl acetate and recrystallised: 3-sulphamoyl-4-phenoxy-5-[β-carbamoylethyl]-benzoic acid, melting point 222°–224° after recrystallisation from methanol/ether. After recrystallisation from ethanol, the melting point is 227°–229°.

The same amide can also be obtained by the following route:

A suspension of 3-sulphamoyl-4-phenoxy-5-aminobenzoic acid (30.8 g=0.1 mol) in 100 ml of glacial acetic acid is brought into solution by adding concentrated hydrochloric acid (24 ml=0.28 mol) at room temperature, the solution is cooled to 5° C. and a solution of sodium nitrite (6.9 g=0.1 mol) in 80 ml of water is added in the course of 15 minutes at 5°–10°, while cooling well and with stirring, and, after stirring for a further 15 minutes at 5° C., 7 g (0.107 mol) of acrylonitrile in 80 ml of acetone and then 5 g (0.03 mol) of copper-II chloride.2H$_2$O are added.

The solution is allowed to warm slowly to room temperature and is then immediately heated with a warm waterbath to 35° C., whereupon an exothermic reaction takes place and a vigorous evolution of nitrogen starts; this evolution of nitrogen is kept within bounds by careful cooling to 35° and has ended after 15 minutes. Acetone is added to the reaction mixture and the resulting mixture is evaporated to dryness, the residue is taken up in ethyl acetate and the solution is washed with dilute sodium chloride solution, dried and filtered and the filtrate is evaporated. After again taking up the residue in ether, separating off insoluble constituents and evaporating the filtrate, crude 3-sulphamoyl-4-phenoxy-5-[β-cyano-β-chloroethyl]-benzoic acid results and this is further processed as follows:

65 g of technical grade zinc dust are added in the course of 15 minutes to 130 g (0.37 mol) of the above chloronitrile, dissolved in 400 ml of glacial acetic acid, the internal temperature rising to 50° C. during the addition, and the mixture is warmed at 80°–85° C. for a further 3 hours. After filtering, washing the material on the filter with glacial acetic acid and evaporating the filtrate, the residue is partitioned between 2 N hydrochloric acid and ethyl acetate. The ethyl acetate layer is washed with water, dried and evaporated, the residue is taken up twice more in benzene and the solution is evaporated and the resulting residue is recrystallised from ethyl acetate: 3-sulphamoyl-4-phenoxy-5-[β-cyanoethyl]-benzoic acid, melting point 212°–216°. The above nitrile can be subjected to acid or alkaline saponification:

(a) Acid saponification: The nitrile (21.2 g) is dissolved (at 20° C.) in 200 ml of concentrated sulphuric acid and the solution is cooled to 5° in an ice bath, 10 g of ice are added, whereupon the temperature rises spontaneously to 30° C., the mixture is left to stand overnight at room temperature, the resulting product is poured onto 2 kg of ice, the mixture is extracted three times with ethyl acetate and, after washing with water and drying, the extract solution is evaporated and the residual brown resin, which is crude 3-sulphamoyl-4-phenoxy-5-[$\beta$-carbamoylethyl]-benzoic acid, is made to crystallise by grinding with ethanol or is further processed direct.

(b) Alkaline saponification: The nitrile (67.8 g = 0.195 mol) is suspended in 970 ml of water at room temperature and a total of 16.5 g of sodium bicarbonate is added carefully in portions. The first third of a total of 390 ml of hydrogen peroxide (30% strength) is added at room temperature to the resulting solution and the pH is adjusted to 8 with a little 2 N sodium carbonate solution. This solution is warmed to 60° for 2 hours, during which time oxygen is evolved, and thereafter precisely the same procedure is followed with the second and, finally, the third third of the hydrogen peroxide. (The pH of the solution is adjusted to 8 each time). After standing overnight, a small amount of manganese dioxide is added in portions in the course of 2 hours, in order to decompose excess hydrogen peroxide, and the remaining peroxide is destroyed with a little solid sodium bisulphite.

The whole is then rendered weakly acid and extracted with ethyl acetate, the ethyl acetate is evaporated and the residue is recrystallised from ethanol. 3-Sulphamoyl-4-phenoxy-5-[$\beta$-carbamoylethyl]-benzoic acid, melting point 227°–229°.

3-Sulphamoyl-4-phenoxy-5-[$\beta$-carbamoyl-ethyl]-benzoic acid (32 g = 0.088 mol), obtained in one or other of the manners described, is dissolved in methanol (450 ml), bromine (14.8 g = 4.75 ml = 0.93 mol) is added at 3° C. and the mixture is stirred for a further 15 minutes at 3°–5°. A sodium methylate solution prepared from 12.2 g of sodium and 500 ml of methanol is then poured in, whereupon the temperature rises to 15° C. The mixture is refluxed for 30 minutes and evaporated to dryness, the residue is dissolved in 500 ml of ice/water, 10 g of sodium bisulphite are added and the mixture is rendered acid with 6 N hydrochloric acid. The resulting suspension is freed from sulphur dioxide in a rotary evaporator and extracted with ethyl acetate. The residue contains crude 3-sulphamoyl-4-phenoxy-5-[$\beta$-(methoxycarbonylamino)-ethyl]-benzoic acid, which can be reacted further direct or can be recrystallised from a little ethyl acetate: melting point 192°–196°.

The above urethane (4.2 g) is dissolved in 50 ml of 2 N sodium hydroxide solution, the solution is warmed at 80° for 6 hours and after cooling is acidified with 6 N hydrochloric acid and extracted with ethyl acetate, and the aqueous phase is concentrated to 40 ml, whereupon 3-sulphamoyl-4-phenoxy-5   -[$\beta$-aminoethyl]-benzoic acid hydrochloride crystallises out. The crystals are filtered off and washed with a little alkanol and ether. The mother liquor is evaporated to dryness, the residue is extracted with ethanol and the extract is also evaporated. The crude products thus obtained can be combined and recrystallised from methanol/ether. The pure 3-sulphamoyl-4-phenoxy-5-[aminoethyl]-benzoic acid hydrochloride melts at 263°–273° with decomposition and partial sublimation.

EXAMPLE 3:

3-Sulphamoyl-4-phenoxy-5-[$\gamma$-(1-pyrrolyl)-propyl]-benzoic acid 2,5-Dimethoxytetrahydrofurane (4.5 g) is added to a solution of 3-sulphamoyl-4-phenoxy-5-[$\gamma$-aminopropyl]-benzoic acid hydrochloride (9.7 g = 25 mmols) in hexamethylphosphoric acid triamide ("Hexametapol"; 50 ml), at 110° under a $N_2$ blanketing gas, and the mixture is kept at this temperature for 2 hours. After cooling, the black solution is poured into 500 ml of ice-water, the mixture is stirred with ethyl acetate (200 ml) and filtered, the filtrate is shaken and, after washing with water, the ethyl acetate layer is extracted with 2 N sodium hydroxide solution, which latter step should be carried out rapidly, and the alkaline extract is acidified with dilute hydrochloric acid.

The resinous residue which precipitates can again be purified by dissolving in ethyl acetate and extracting with sodium hydroxide solution. After recrystallisation from chloroform/cyclohexane, pure 3-sulphamoyl-4-phenoxy-5-[$\gamma$-(1-pyrrolyl)-propyl]-benzoic acid with a melting point of 178°–180° C. is obtained.

The amine used as the starting material is obtained from 3-sulphamoyl-4-phenoxy-5-[$\beta$-cyanoethyl]-benzoic acid, which has been described in Example 2, by catalytic hydrogenation, as follows:

The nitrile (3.46 g) is dissolved in 70 ml of methanol saturated with ammonia, the solution is after-saturated for 30 minutes under an ammonia pressure of 5 bars and, after adding 1 g of Raney Ni, is hydrogenated for 12 hours at 70°–80° C. and under an initial hydrogen pressure of 100 bars. The catalyst is then filtered off and washed with methanol and the filtrate is evaporated. After taking up the residue in a little water, the solution is acidified and extracted by shaking with ethyl acetate and the acid aqueous phase is again evaporated, dried and extracted with ethanol, the ethanol extract is concentrated to 30 ml and ether is added: 3-sulphamoyl-4-phenoxy-5-[$\gamma$-aminopropyl]-benzoic acid hydrochloride crystallises out; melting point 259°–262° C.

EXAMPLE 4

3-Sulphamoyl-4-phenoxy-5-[$\beta$-(1-pyrrolyl)-isopropyl)[-benzoic acid

Hexamethylphosphoric acid triamide ("Hexametapol"; 50 ml) is poured over 3-sulphamoyl-4-phenoxy-5-[$\beta$-aminoisopropyl]-benzoic acid (9.7 g = 25 mmols) under nitrogen, the mixture is heated to 115° C. and 4.5 g of 2,5-dimethoxytetrahydrofurane are added, the resulting mixture is kept at this temperature for one hour and poured into 200 ml of ice-water and this mixture is acidified with 2 N hydrochloric acid and extracted with ethyl acetate. The ethyl acetate solution, which has been filtered to remove insoluble constituents, is twice extracted with saturated bicarbonate solution with the addition of sodium chloride solution, the aqueous phase is again acidified with 6 N hydrochloric acid, the precipitate is again taken up in ethyl acetate and the solution is evaporated to dryness.

The resulting resin is purified by dissolving it in ethyl acetate, adding ether to the solution, filtering with the addition of Hyflo and evaporating the filtrate and is recrystallised from chloroform/cyclohexane: small beige-coloured leaves with a melting point of 194°–199° C.

The starting material is obtained as follows: glacial acetic acid (150 ml) is poured over 3-sulphamoyl-4-phenoxy-5-aminobenzoic acid (P. W. Feit, J. Med. Chem. 14, 432 (1971); 46.8 g) at room temperature and concentrated hydrochloric acid (36 ml) is added to the mixture, whereupon the temperature rises to 30°. The yellow-red solution is cooled to 0°-5° C. and diazotised (for 30 minutes), with cooling, by adding a solution of 10.5 g of sodium nitrite in 50 ml of water, the reaction mixture is stirred for a further 15 minutes at 0°-5° C. and then added all at once to a solution of methacrylamide (16.3 g = 195 mmols) in 120 ml of acetone, whereupon the temperature rises to 18° C. After adding copper-II chloride dihydrate (7.5 g) in 10 ml of water, the resulting suspension is carefully brought to 35° C., whereupon a vigorous evolution of nitrogen starts, which has to be moderated by cooling. The evolution of gas ceases after 10 minutes and the solution is stirred for a further 15 minutes and evaporated in vacuo. 2 N hydrochloric acid and ethyl acetate are added to the residue, the mixture is filtered, the phases are separated and, after washing with water and drying, the ethyl acetate phase is evaporated. The residue is recrystallised from a little ethyl acetate and washed with petroleum ether: 3-sulphamoyl-4-phenoxy-5-[$\beta$-carbamoyl-$\beta$-chloroisopropyl]-benzoic acid; melting point 233°-237° C.

20.7 g of this compound are suspended in 60 ml of glacial acetic acid, the suspension is heated to 85° C. and 10 g of zinc dust are added in the course of 15 minutes, whereupon the temperature rises to a maximum of 105° C. After further heating at 90° (for 3 hours), the mixture is filtered hot, the material on the filter is washed with glacial acetic acid and the filtrate is evaporated in vacuo. The pale yellow, viscous residue is extracted with ethyl acetate and the solution is washed with water, dried and concentrated to a small volume, whereupon crystallisation takes place: 3-sulphamoyl-4-phenoxy-5-[$\beta$-carbamoylisopropyl]-benzoic acid, melting point 223°-226° C.

The above amide (36.8 g = 0.0975 mol) is dissolved at room temperature in a mixture of 800 ml of methanol and 100 ml of dioxane and, after cooling the solution to 0°, bromine (23.4 g = 7.45 ml = 0.146 mol) is added, the mixture is stirred for a further 15 minutes at 0°-5°, a sodium methylate solution prepared from 9.2 g of sodium and 500 ml of methanol is added, whereupon the temperature rises to 15° C., and the mixture is refluxed for 30 minutes and evaporated in vacuo.

The honey-like, pale yellow residue is dissolved in 500 ml of ice-water, 20 g of sodium bisulphite are added, the mixture is acidified with 6 N hydrochloric acid, whereupon excess sulphur dioxide escapes, and the colourless precipitate which separates out is taken up in ethyl acetate by extracting by shaking. The ethyl acetate phase is separated off, washed twice with water, filtered, dried and evaporated. The resulting syrup which does not tend to crystallisation and consists of 3-sulphamoyl-4-phenoxy-5-[$\beta$-(methoxycarbonylamino)-isopropyl]-benzoic acid is further processed without further purification.

The above urethane (40.9 g) is dissolved in 400 ml of 2 N sodium hydroxide solution and the solution is warmed to 80° and kept at this temperature for 8 hours. It is cooled and extracted with ether and the aqueous phase is acidified in the cold with concentrated hydrochloric acid. The acid aqueous phase is freed from organic impurities by shaking with ethyl acetate, shaking with active charcoal and filtering through Hyflo and is evaporated to dryness in vacuo, the residue is twice stirred with a little ethanol and benzene and the solution is evaporated and the final residue is twice boiled thoroughly with ethanol and the combined ethanol extracts are concentrated to a small volume, whereupon crystallisation starts: 3-sulphamoyl-4-phenoxy-5-($\beta$-aminoisopropyl)-benzoic acid hydrochloride; crystals which melt above 275° C. (from ethanol/ether).

EXAMPLE 5

3-Sulphamoyl-4-phenylthio-5-[$\gamma$-(1-pyrrolyl)-propyl]-benzoic acid 1.86 g 3-Sulphamoyl-4-phenylthio-5-[$\gamma$-aminopropyl]-benzoic acid hydrochloride are suspended in 10 ml of hexamethylphosphoric acid triamide ("Hexametapol"), under nitrogen blanketing gas, the suspension is heated to 110° and 0.7 g of 2,5-dimethoxytetrahydrofurane is added with stirring, whereupon a brown solution forms. After one hour, the solution is cooled and poured onto ice, the mixture is extracted by shaking with ethyl acetate and filtered, the aqueous phase is again extracted with ethyl acetate and, after washing with water and drying, the combined ethyl acetate extracts are evaporated in vacuo. The crude product, which crystallises spontaneously, is again taken up in ethyl acetate, petroleum ether is added, brown flocks are filtered off over Hyflo and the filtrate is concentrated and crystallised by carefully adding petroleum ether. The compound, which is already very pure, can be recrystallised again from chloroform/cyclohexane: melting point 184°-187° (decomposition).

The starting material is accessible by the following route: 4.8 ml of concentrated hydrochloric acid and 20 ml of water are added to 3-sulphamoyl-4-chloro-5-aminobenzoic acid (P. W. Feit, H. Bruun and C. Kaergaard-Nielsen, J. Med. Chem. 13, 1,071 (1970); 5.01 g = 20 mmols) and the resulting slurry is cooled to +3° C. and diazotised with 20 ml of 1 N sodium nitrite solution at 0°-5°, after which, after a total of 30 minutes, a solution of acrylonitrile (1.4 g = 1.74 ml = 26 mmols) in acetone (25 ml) is added to the suspension, which has become mobile, and solid $CuCl_2.2H_2O$ (1 g) is added to the resulting yellow solution, carefully at first and then all at once, and the mixture is heated slowly to 35° C., with vigorous stirring, whereupon a vigorous evolution of nitrogen starts fairly suddenly; this has ended after about 15 minutes. After a further 15 minutes, flocks are filtered off and the filtrate is cooled to +5° C., whereupon a dark resin settles on the base of the flask, the supernatant solution is decanted off from the resin and latter is ground with 30 ml of water. After it has been taken up in 200 ml of ethyl acetate the acid is extracted with sodium bicarbonate solution and the acid is precipitated by acidifying the extract and is taken up in ethyl acetate again. For further purification, the dried ethyl acetate solution is filtered through a column containing 35 g of silica gel, the filtrate is evaporated in vacuo and the residue is further processed. The above crude product comprising 3-sulphamoyl-4-chloro-5-($\beta$-chloro-$\beta$-cyanoethyl)-benzoic acid (2.7 g = 8.35 mmols) is dissolved in glacial acetic acid and a total of 1.5 g of zinc dust is added in portions at room temperature, with stirring, the temperature slowly rising during the addition. After 20 minutes, the temperature is raised to 90°-100° for 45 minutes, the resulting suspension is then filtered and the precipitate is washed with glacial acetic acid and the filtrate is evaporated in vacuo. The residue is acidified with hydrochloric acid and extracted with ethyl acetate and the resulting solution is concentrated to a smaller volume and crystallised. The resulting 3-sulphamoyl-4-chloro-5-($\beta$-cyanoethyl)-benzoic acid melts at 224°-228° C. This compound (72 g=0.25 mol) is added, under nitrogen blanketing gas, to a thiophenolate solution prepared from solid sodium hydroxide (25 g=0.625 mol), water (30 ml) and thiophenol (68.8 g=63.7 ml=0.625 mol) and the resulting suspension is dissolved by adding 150 ml of hexamethylphosphoric acid triamide, the temperature spontaneously rising to above 100°. The mixture is kept at 110° (reflux) for a further 5 hours and is then poured into 300 ml of water, rendered strongly acid (Congo red) with 6 N hydrochloric acid and extracted three times with ethyl acetate, the ethyl acetate layer is separated off and washed twice with sodium chloride solution and is twice extracted by shaking with saturated sodium bicarbonate solution and twice extracted by shaking with water (excess thiophenol remains in the ethyl acetate phase), the combined bicarbonate and water phases are acidified, the precipitate which has separated out is again taken up in ethyl acetate, the ethyl acetate layer is washed with water, dried and filtered and the filtrate is evaporated. On grinding with a little ethyl acetate, 3-sulphamoyl-4-phenylthio-5-[$\beta$-cyanoethyl]-benzoic acid crystallises; pale yellow crystals from ethyl acetate/ether, melting point 179°-181° C.

The above nitrile (34.3 g=0.0946 mol) is hydrogenated in glacial acetic acid (350 ml) over prehydrogenated platinum oxide (6 g) under normal pressure in the course of 74 hours, the catalyst being added in three equal portions: before the hydrogenation, after the absorption of 2% of the theoretical amount of hydrogen and after the absorption of 74% of the theoretical amount of hydrogen. The catalyst is filtered off, excess 6 N hydrochloric acid is added to the filtrate, the mixture is evaporated to dryness and the residue is twice taken up in ethanol and benzene and evaporated to dryness; brown crystals, which are boiled thoroughly with methanol and recrystallised from ethanol with the addition of ether: 3-sulphamoyl-4-phenylthio-5-[$\gamma$-aminopropyl]-benzoic acid hydrochloride, melting point>300° C. (decomposition).

EXAMPLE 6

3-Sulphamoyl-4-phenoxy-5-(2,5-dimethyl-1-pyrrolyl)-benzoic acid

A mixture of 3-sulphamoyl-4-phenoxy-5-aminobenzoic acid (1.54 g=5 mmols; P. W. Feit, J. Med. Chem. 14, 432 (1971)), acetonylacetone (0.57 g=5 mmols) and 10 ml of glacial acetic acid is refluxed under N$_2$ for 30 minutes, the red reaction solution is evaporated in vacuo and freed from residues of glacial acetic acid and water by adding benzene and evaporating azeotropically, the residue is dissolved in acetone, the solution is boiled with silica gel and filtered through a fine filter and the solution is concentrated to 50 ml and, after adding 50 ml of ethyl acetate, freed from acetone residues in vacuo, whereupon crystallisation takes place. After the purification procedure has been repeated, beige-coloured crystals with a melting point of 283°-286° (decomposition) result.

EXAMPLE 7

3-Sulphamoyl-4-phenoxy-5-[$\beta$-(2,5-dimethyl-1-pyrrolyl)-ethyl]-benzoic acid.

A mixture of 3-sulphamoyl-4-phenoxy-5-[$\beta$-aminoethyl]-benzoic acid (5.0 g=1.35 mmols; see Example 3 for the preparation), acetonylacetone (1.85 g, approximately 16.2 mmols) and hexamethylphosphoric acid triamide (Hexametapol; 25 ml) is warmed at 100° for 30 minutes under N$_2$ in an apparatus which has been protected against incident light by covering it with aluminium foil, and the reaction solution is worked up as follows, with strict exclusion of light throughout: pouring into ice-water (50 ml) and extracting with ethyl acetate, washing the extract with water, drying and filtering and evaporating the filtrate. The crude product is recrystallised from chloroform/cyclohexane with the addition of active charcoal and gives pale orange-coloured, light-sensitive crystals, melting point>210° (decomposition).

EXAMPLE 8

3-Sulphamoyl-4-phenylthio-5-[$\beta$-(1-pyrrolyl)-ethyl]-benzoic acid

3-Sulphamoyl-4-chloro-5-[$\beta$-(1-pyrrolyl)-ethyl]-benzoic acid (16 g=30 mmols) is dissolved in hexamethylphosphoric acid triamide (Hexametapol; 60 ml), the solution is added at room temperature to a solution prepared from thiophenol (8.8 g=8 ml), sodium hydroxide (4.8 g) and water (10 ml) and the mixture is heated to 130° C. for 8 hours under nitrogen blanketing gas with slow removal of water and excess thiophenol and is then poured into ice-water and acidified with 2 N hydrochloric acid. After repeated extraction with ethyl acetate, washing of the extract solution with water, extraction of the acid with bicarbonate solution, acidification of the extract and again taking up the product in ethyl acetate, drying and adding cyclohexane, a crude product is obtained which, after recrystallising twice from ethyl acetate/chloroform/petroleum ether, melts at 191°-193°.

The starting material, i.e. 3-sulphamoyl-4-chloro-5-[$\beta$-(1-pyrrolyl)-ethyl]-benzoic acid, is obtained as follows: zinc dust (1.5 g) is added in portions to 3-sulphamoyl-4-chloro-5-($\beta$-chloro-$\beta$-cyanoethyl)-benzoic acid (prepared from 3-sulphamoyl-4-chloro-5-amino-benzoic acid, 2.7 g, see Example 5) in glacial acetic acid (10 ml), the temperature rising to a maximum of 40° during the addition, and after 30 minutes the mixture is warmed at 90°-100° for a further three quarters of an hour, with stirring, and, finally, the mixture is filtered, the material on the filter is washed with glacial acetic acid, the filtrate is evaporated and, after acidifying with 2 N hydrochloric acid, the evaporation residue is taken up in ethyl acetate and crystallised by grinding: 3-sulphamoyl-4-chloro-5-($\beta$-cyanoethyl)-benzoic acid, melting point 224°-228° C.

The above nitrile (8.65 g=30 mmols) is added to a mixture, which has been cooled to 5° C., of 100 ml of concentrated sulphuric acid and 5 g of ice, the resulting clear solution is left to stand at room temperature for 8 hours and poured onto 800 g of ice and the precipitate which separates out is filtered off. After recrystallisation from a little methanol, the 3-sulphamoyl-4-chloro-5-($\beta$-carbamoylethyl)-benzoic acid melts at 251-254° C. (decomposition).

The above amide (1.5 g=5 mmols) is suspended in methanol (30 ml) and the suspension is cooled to 0°–5° C., bromine (800 mg=2.54 ml=10 mmols) and then a sodium methylate solution prepared from 690 mg of sodium and 30 ml of methanol are added and the resulting solution, after standing in an ice-bath for a quarter of an hour, is refluxed for half an hour; after adding water, excess solid sodium bisulphite is first added and, after some time, the mixture is carefully acidified with 2 N hydrochloric acid and, after partially evaporating in vacuo, extracted with ethyl acetate, the ethyl acetate solution is treated with active charcoal and filtered and the filtrate is concentrated somewhat, whereupon crude 3-sulphamoyl-4-chloro-5-(β-methoxycarbonylaminoethyl)-benzoic acid crystallises out; melting point 200°–210° C.

The above urethane (22 g=66 mmols) in 100 ml of 2 N sodium hydroxide solution is warmed at 80° C. for two hours, the solution is acidified and extracted with ethyl acetate, the aqueous phase is evaporated, the residue is twice taken up in ethanol and the solution is evaporated to dryness and the resulting crude 3-sulphamoyl-4-chloro-5-(β-aminoethyl)-benzoic acid hydrochloride is purified by recrystallisation from ethanol/ether: melting point 254°–256° C.

The above hydrochloride (3.15 g=10 mmols) is suspended in 20 ml of hexamethylphosphoric acid triamide (Hexametapol), the suspension is heated to 90°–100° C., 2,5-dimethoxytetrahydrofurane (1.4 g=11 mmols) is added and after a reaction time of one hour the mixture is cooled, poured onto ice (100 g) and extracted three times with ethyl acetate, the solution is washed with water, dried with sodium sulphate, decolorised with silica gel and filtered and the filtrate is concentrated to 100 ml, treated with active charcoal and filtered until fibre-free, and the resulting filtrate is concentrated to 20 ml and crystallised: 3-sulphamoyl-4-chloro-5-[β-(1-pyrrolyl)-ethyl]-benzoic acid, melting point 224°–225° C.

I claim:

1. A 4-substituted 3-sulphamoyl-5-pyrrolylalkylbenzoic acid of the formula I

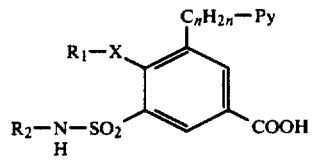

in which $R_1$ is phenyl or phenyl substituted by lower alkyl, lower alkoxy, halogeno, trifluoromethyl and/or amino, X is oxygen or sulphur, $R_2$ is hydrogen, lower alkyl, lower alkoxymethyl or $R_1$, Py is 1-pyrrolyl or 1-pyrrolyl substituted by lower alkyl and n is an integer from 1 to 4; or a therapeutically useful, non-toxic salt thereof.

2. A compound of the formula I according to claim 1, in which Py is 1-pyrrolyl which is unsubstituted or substituted by lower alkyl in the 3- and/or 4-position, n is an integer from 1 to 4, $R_1$ is phenyl, lower alkyl-phenyl, lower alkoxy-phenyl or halogenophenyl, X is oxygen or sulphur and $R_2$ is hydrogen, lower alkyl or lower alkoxymethyl.

3. A compound of the formula I according to claim 1, in which Py is 1-pyrrolyl, n is an integer from 1 to 3, $R_1$ is phenyl, X is oxygen or sulphur and $R_2$ is hydrogen.

4. A compound of the formula I according to claim 1, in which $R_1$ is phenyl, $R_2$ is hydrogen, X is oxygen, Py is 2,5-dimethyl-1-pyrrolyl.

5. A compound of the formula I according to claim 1, in which $R_1$ is phenyl, $R_2$ is hydrogen, X is oxygen, Py is 1-pyrrolyl and n is 2 or 3.

6. A compound of the formula I according to claim 1, in which $R_1$ is phenyl, $R_2$ is hydrogen, X is sulfur, Py is 1-pyrrolyl and n is 2 or 3.

7. A compound of the formula I according to claim 1, in which $R_1$ is phenyl, $R_2$ is hydrogen, X is oxygen, Py is 2,5-dimethyl-1-pyrrolyl and n is 2.

8. A compound of the formula I according to claim 1, in which $R_1$ is phenyl, $R_2$ is hydrogen, X is oxygen, Py is 1-pyrrolyl and $C_nH_{2n}$ is isopropyl.

9. A diuretic pharmaceutical formulation containing a diuretically effective amount of a compound of of the formula I claimed in claim 1, together with a pharmaceutically usable excipient.

10. The method of treating high blood pressure of edema in mammals, which comprises administering to said mammals enterally or parenterally an effective amount of a compound of the formula I claimed in claim 1, as diuretic acid saluretic agent.